(12) United States Patent
Davis

(10) Patent No.: US 9,352,170 B1
(45) Date of Patent: May 31, 2016

(54) SPECTRAL LIGHT THERAPY FOR AUTISM SPECTRAL DISORDERS

(71) Applicant: Christina Davis, Warminster, PA (US)

(72) Inventor: Christina Davis, Warminster, PA (US)

(*) Notice: Subject to any disclaimer, the term of this patent is extended or adjusted under 35 U.S.C. 154(b) by 0 days.

(21) Appl. No.: 13/754,277

(22) Filed: Jan. 30, 2013

Related U.S. Application Data

(60) Provisional application No. 61/592,751, filed on Jan. 31, 2012.

(51) Int. Cl.
*A61N 5/06* (2006.01)

(52) U.S. Cl.
CPC .......... *A61N 5/0618* (2013.01); *A61H 2201/10* (2013.01); *A61N 2005/0663* (2013.01)

(58) Field of Classification Search
CPC ............... A61N 2005/0663; A61N 5/0618; A61H 2201/10; F21Y 2113/002; F21Y 2113/005; B60Q 3/02; B64D 2011/0038
USPC .................................. 607/88–91, 81
See application file for complete search history.

(56) References Cited

U.S. PATENT DOCUMENTS

| | | | |
|---|---|---|---|
| 5,824,024 A * | 10/1998 | Dial | 607/88 |
| 6,602,275 B1 * | 8/2003 | Sullivan | 607/88 |
| 7,001,413 B2 | 2/2006 | Butler | |
| 7,081,128 B2 | 7/2006 | Hart et al. | |
| 7,087,074 B2 | 8/2006 | Hasegawa | |
| 7,118,589 B2 | 10/2006 | Vlahos | |
| 7,125,416 B2 | 10/2006 | Kent et al. | |
| 7,147,319 B2 | 12/2006 | Lin | |
| 7,201,766 B2 | 4/2007 | Butler | |
| 7,253,824 B2 | 8/2007 | Medes et al. | |

(Continued)

FOREIGN PATENT DOCUMENTS

| | | |
|---|---|---|
| WO | WO 2006/101735 A1 | 9/2006 |
| WO | WO 2010/076710 A1 | 7/2010 |

(Continued)

OTHER PUBLICATIONS http://lightenergystudio.com/flash/modular_wall_units/LED_dome_panels.html archived on Dec. 16, 2010 (retrieved on Jan. 8, 2015), backdated using the Internet Archive Wayback Machine <URL:http://web.archive.org/web/20101216182907/http://lightenergystudio.com/flash/modular_wall_units/LED_dome_panels.html>.* http://www.ledlightsheet.com/ledlb.html archived on Aug. 6, 2010 (retrieved on Jan. 9, 2015), backdated using the Internet Archive Wayback Machine <URL:http://web.archive.org/web/20100806201403/http://www.ledlightsheet.com/ledlb.html>.*

(Continued)

*Primary Examiner* — Lynsey Crandall
*Assistant Examiner* — Nathan J Jenness
(74) *Attorney, Agent, or Firm* — Howson and Howson LLP

(57) ABSTRACT

A spectral color and light therapy system is described which is useful in treating mood, anxiety, attention, substance, and/or behavioral disorders. The system utilizes one or more light source which emits visible colored light at a brilliance factor of at least about 2500 and at least one of four colors which are different from each other, said system providing (a) (i) a light source emitting blue light in the range of about 450 to about 475 nm; and (ii) a source emitting green visible light in the range of about 495 nm to about 570 nm; and (b) a light source emitting rose pink light in the range of about 635 nm to about 650 nm; and a light source of peach light in the range of about 590 nm to about 630 nm. Also provided are methods of treating mood, anxiety, attention, substance, and/or behavioral disorders. Methods of treating and/or ameliorating the symptoms of autism spectrum disorders are described.

8 Claims, 4 Drawing Sheets

(56) References Cited

U.S. PATENT DOCUMENTS

| | | | |
|---|---|---|---|
| 7,288,257 | B2 | 10/2007 | Powell |
| 7,303,578 | B2 | 12/2007 | De Taboada et al. |
| 7,309,348 | B2 | 12/2007 | Streeter et al. |
| 7,374,569 | B2 | 5/2008 | Whatcott et al. |
| 7,534,255 | B1 | 5/2009 | Streeter et al. |
| 7,537,576 | B1 | 5/2009 | Worley, III |
| 7,654,949 | B2 | 2/2010 | McNew |
| H2242 | H | 7/2010 | Gonzales |
| 7,758,872 | B1 | 7/2010 | Finzi |
| 7,763,059 | B2 | 7/2010 | Perez |
| 7,815,668 | B2 | 10/2010 | Butler |
| 7,842,075 | B2 | 11/2010 | Kahn et al. |
| 7,850,720 | B2 | 12/2010 | Shefi et al. |
| 7,959,587 | B2 | 6/2011 | Worley |
| 2005/0185399 | A1* | 8/2005 | Beermann et al. ............ 362/231 |
| 2006/0064144 | A1* | 3/2006 | Chen et al. ...................... 607/90 |
| 2010/0249036 | A1 | 9/2010 | Finzi |
| 2010/0292746 | A1 | 11/2010 | Gorham |
| 2010/0318161 | A1 | 12/2010 | Brawn |
| 2010/0329524 | A1 | 12/2010 | Swartling |
| 2010/0331929 | A1 | 12/2010 | Burrows et al. |
| 2011/0009464 | A1 | 1/2011 | Chen |
| 2011/0034971 | A1 | 2/2011 | Svanberg et al. |
| 2011/0040356 | A1 | 2/2011 | Schiffer |
| 2011/0066213 | A1 | 3/2011 | Huttermann et al. |
| 2011/0125230 | A1 | 5/2011 | Friedman et al. |
| 2011/0143286 | A1 | 6/2011 | Takada et al. |
| 2011/0144723 | A1 | 6/2011 | Streeter et al. |
| 2011/0152967 | A1 | 6/2011 | Simon et al. |
| 2012/0206050 | A1* | 8/2012 | Spero ............................. 315/152 |

FOREIGN PATENT DOCUMENTS

| | | |
|---|---|---|
| WO | WO 2010/092501 A1 | 8/2010 |
| WO | WO 2010/127249 A1 | 11/2010 |

OTHER PUBLICATIONS

Berman et al., Photopic Luminance Does Not Always Predict Perceived Room Brightness, Lighting Research and Technology, vol. 22, No. 1, pp. 150-165, (Mar. 1990).

Boray et al., Effects of Warm White, Cool White and Full Spectrum Fluorescent Lighting on Simple Cognitive Performance, Mood and Ratings of Others, Journal of Environmental Psychology, 9, pp. 297-308, (1989).

Berman et al., Luminance-Controlled Pupil Size Affects Landolt C Task Performance, Journal of the Illuminating Engineering Society, 22, pp. 150-165 (Feb. 1993).

Czeisler et al., Exposure to Bright Light and Darkness to Treat Physiologic Maladaptation to Night Work, The New England Journal of Medicine, vol. 332, No. 18 pp. 1253-1259, (May 3, 1990).

Jacobsen et al., Seasonal Affective Disorder: A review of the Syndrome and it Public Health Implications, American Journal of Public Health, vol. 77, No. 1, pp. 57-60, (Jan. 1987).

Lam, Light Therapy for Seasonal Bulimia, American Journal of Psychiatry, 146(12), pp. 1640-1641, (Dec. 1989).

London, Full-Spectrum Classroom Light and Sickness in Pupils, The Lancet, pp. 1205-1206, (Nov. 21, 1987).

Rosenthal et al., Antidepressant Effects of Light in Seasonal Affective Disorder, American Journal of Psychiatry, 142, pp. 163-170 (Feb. 1985).

Saslow, L.I. Schools Test New Lights to Reduce Glare, The New York Times, pp. 1-2 (Mar. 3, 1991).

Veitch et al., Demand Characteristics and Full Spectrum Lighting Effects on Performance and Mood, Journal of Environmental Psychology, 11, pp. 87-95, (1991).

Wurtman & Wurtman, Carbohydrates and Depression, Scientific America, pp. 68-75, (Jan. 1989).

\* cited by examiner

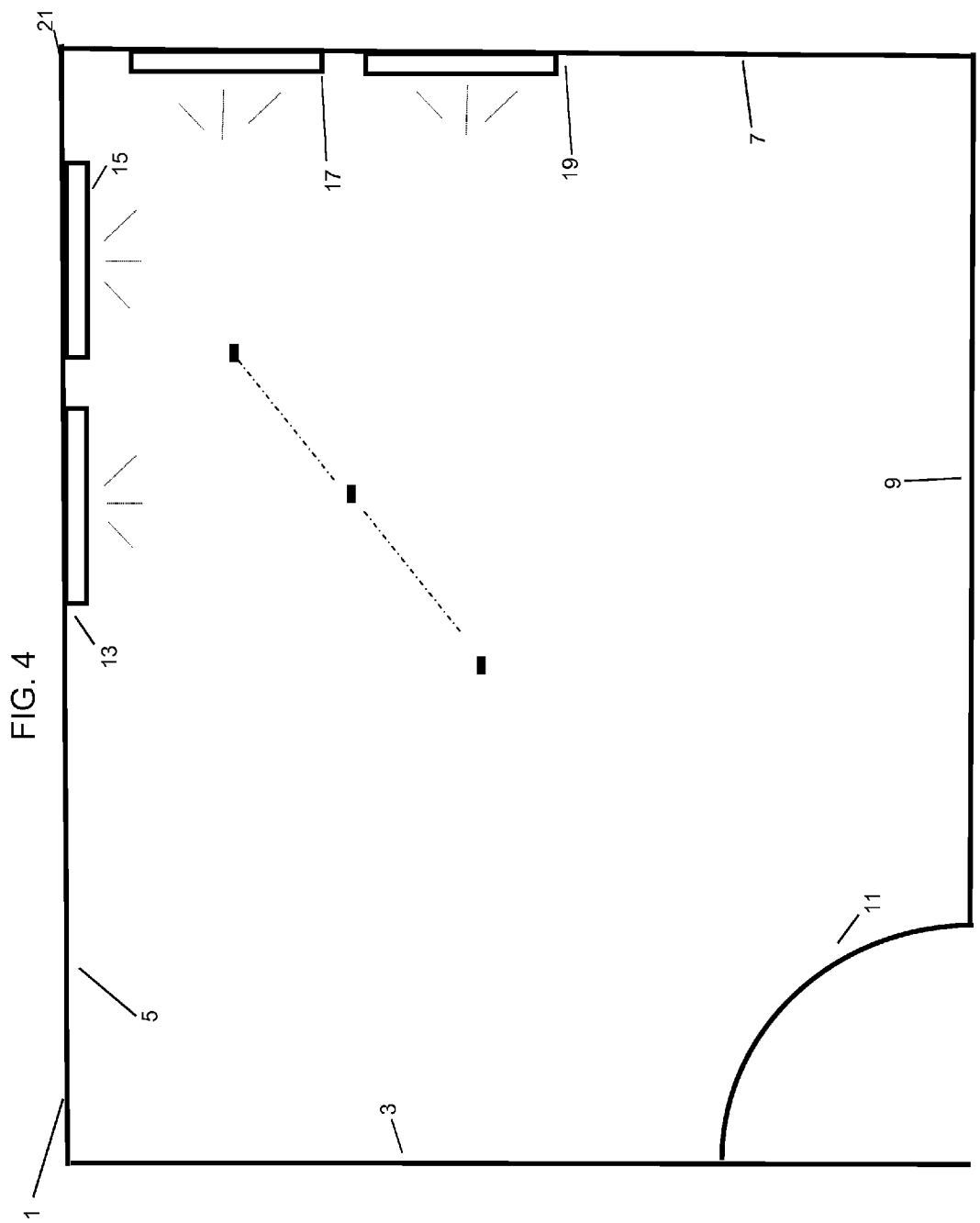

SPECTRAL LIGHT THERAPY FOR AUTISM SPECTRAL DISORDERS

BACKGROUND OF THE INVENTION

The experimental use of light in combination with Albert Einstein's Quantum nature of light, based on the work of Philippe Lenard on the wavelength theory (1905) won him his only Nobel Prize in 1921.

The research of Thomas Young 102 years prior to these two men showed that light is made of waves. Waves spread out whereas light particles are contained in one place. Einstein demonstrated this using the photoelectric effect, that light is made of particles, or photons, and that the photons of high-frequency light have more energy than the photons of low-frequency light.

In Einstein's theory, each photon of a given color, i.e. green, has a certain amount of energy. Reducing the intensity of a beam of green light only reduces the number of photons in the beam. Each remaining photon still has the same amount of energy as any other photon of green light.

These researchers and others delved into the organic properties of light. Color became the major influence to begin utilizing the color combinations that changed moods, promoted relaxation, altered negative behavior and perception through penetration of the correct colored light wavelengths absorbed by the photoreceptors of the eye, and the responsiveness of the frontal and temporal lobes to this new therapeutic combination. Neil Bohr, Shealy, Babbitt and Dr. Ott have all researched various organic effects of colors.

What are still needed are non-invasive methods for treating autism spectral disorders.

SUMMARY OF THE INVENTION

In one aspect, the invention provides a spectral color and light therapy system. The system comprises one or more light source which emits visible colored light at a brilliance factor of at least about 2500 LUX and contains four colors which are different from each other. The system comprises (i) a light source emitting blue light in the range of about 450 to about 475 nm; (ii) a source emitting green visible light in the range of about 495 nm to about 570 nm; and (b) a light source emitting rose pink light in the range of about 635 nm to about 650 nm; and a light source of peach light in the range of about 590 nm to about 630 nm.

In another aspect, the invention provides a therapy room comprising a color and light therapy system as described herein. The room comprises two to four walls and an entrance, wherein the system is positioned in a corner which is located most distant from the entrance.

In yet another aspect, the invention provides a method for treating mood, anxiety, attention, substance, and/or behavioral disorders comprising positioning a subject to see at least one, at least two, or the four light sources for a sufficient amount of time to provide a therapeutic or mood-altering benefit. In one embodiment, the subject is positioned so as to see blends of a first pair of lights, the second pair of lights, or a blend of the first pair and second pair of lights. Preferably the treatment is in a therapy room which is white, sunlight gold, or pale blue.

In still another aspect, the invention provides a method for treating and/or ameliorating the symptoms of an autism spectrum disorder comprising positioning a subject to see at least one, at least two, or the four light sources for a sufficient amount of time to provide a therapeutic or mood-altering benefit. In one embodiment, the subject is positioned so as to see blends of a first pair of lights, the second pair of lights, or a blend of the first pair and second pair of lights. Preferably the treatment is in a therapy room which is white, sunlight gold, or pale blue.

Still other aspects and advantages of the invention will be apparent from the following detailed description of the invention.

BRIEF DESCRIPTION OF THE DRAWINGS

FIG. 4 is a top view of an exemplary color therapy room 1 of the invention. The room has four walls 3, 5, 7 and 9, an entrance 11. The color therapy room contains a color and light therapy system positioned in a corner 21 which is located most distant from the entrance. The illustrated system includes four light sources 13, 15, 17, 19 which emit colored light. A subject receiving therapy may be positioned 18 inches to 6 feet from the first and/or second set of lights.

DETAILED DESCRIPTION OF THE INVENTION

Figure 1:
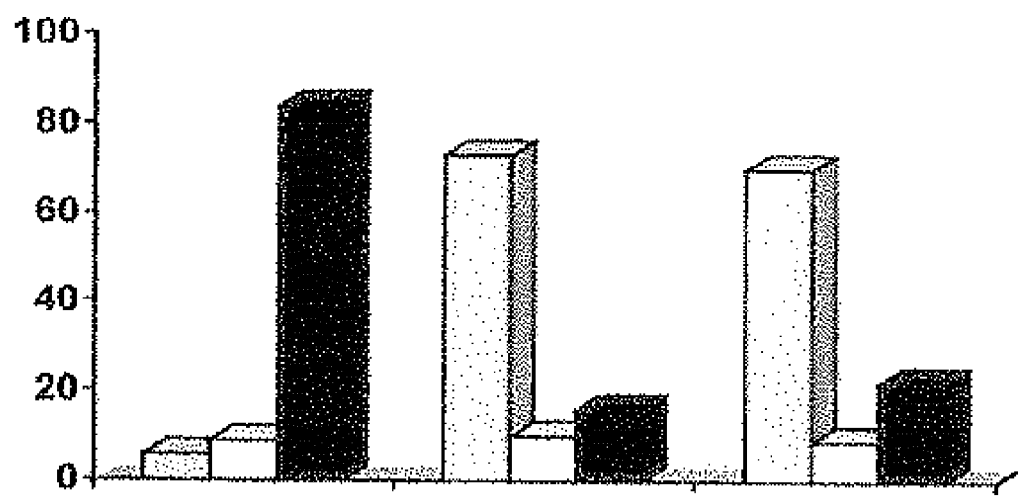
FIG. 1 is a bar chart illustrating the success ratio of the color light therapy of the invention in a series of studies of students and adults with autism and attention deficit hyperactivity disorder (ADHD). The grey columns (first bar) show improvement for anxiety disorders. The white columns (second bar) show the original state upon entrance to the program. The dark columns (third bar) show Improvement after the color light therapy.

In one aspect, the invention provides a spectral color and light therapy system which utilizes a four color system.

As described in the background, the use of seven color system for light therapy has been described. However, in some cases this seven color system shows a counterproductive responsorial outcome in those within the Autistic spectrum who refuse bright light and preferred incandescent lighting or a darkened room. In the system of the present invention, positive therapeutic effects were observed in the absence of any observable counterproductive responsorial outcome caused by the therapy system.

The system comprises one or more light sources which emits visible colored light. Thus, the present invention utilizes the visual ability of a subject. The type of light useful in the present invention is spectral colors of blue, green, rose pink and peach. The wavelength is within the visible spectrum (the range of wavelengths humans can perceive, approximately from 390 nm to 750 nm), it is known as "visible light". See conversion chart below:

| Color | Frequency | Wavelength |
| --- | --- | --- |
| violet | 668-789 THz | 380-450 nm |
| blue | 631-668 THz | 450-475 nm |
| cyan | 606-630 THz | 476-495 nm |
| green | 526-606 THz | 495-570 nm |
| yellow | 508-526 THz | 570-590 nm |
| orange | 484-508 THz | 590-620 nm |
| red | 400-484 THz | 620-750 nm |

Unless otherwise specified, when reference is made to one of the above visible colors, a color within the above range is intended. Useful wavelengths include a variety of wavelengths spanning the ranges identified above. For example, other suitable ranges for red may include a wavelength of about 635 to 700 nm, or 700 nm; for orange a wavelength of about 590 to about 635 nm, or about 620 nm; for yellow a wavelength of about 560 nm to about 590 nm, or about 580 nm; for green a wavelength of about 530 nm, for blue a wavelength of about 470 nm, and for violet a wavelength of about 420 nm.

For the colors used in the spectral system of the invention, the four colors include blends of the above colors. For example, in one embodiment, the "peach light" light source used in the invention is a blend of gold, yellow and orange wavelengths and has a wavelength of about 600 nm, but may vary from about 590 nm to about 630 nm, or about 580 nm to about 610 nm. In another embodiment the "rose pink" light is a blend and has a wavelength of about 545 nm; in other embodiments, this shade may vary from about 635 nm to about 650 nm.

In addition to "peach" and "rose pink", the invention also utilizes blue and green lights. In one embodiment, the blue is selected from within the range provided above. In another embodiment, the blue source contains some green and provides a wavelength of about 500 nm. In still another embodiment, a subject viewing the blue light source also absorbs light from a proximal green light source and absorbs a blended light of about 500 nm. In still a further embodiment, the green selected is within the range provided above, or within the range of about 540 to about 560 nm, or about 550 nm.

Suitably, the spectral color and light therapy system uses light sources which are free of harmful non-visible light emissions, i.e., light of wavelengths below 390 nm or above 750 nm. This may be achieved through the use of known screening gels or other screening devices or selection of appropriate light sources.

In one embodiment, the color and light therapy system also provides for the light system to generate a minimum intensity.

As used herein, lux (symbol: lx) is the International System of Units (SI) unit of illuminance and luminous emittance, measuring luminous flux per unit area. It is used in photometry as a measure of the intensity, as perceived by the human eye, of light that hits or passes through a surface. It is analogous to the radiometric unit watts per square meter, but with the power at each wavelength weighted according to the luminosity function, a standardized model of human visual brightness perception. One lux is equal to one lumen per square meter: 1 lx=1 lm/m$^2$=1 cd·sr·m$^{-2}$. A flux of 1,000 lumens, concentrated into an area of one square meter, lights up that square meter with an illuminance of 1,000 lux. However, the same 1,000 lumens, spread out over ten square meters, produces a dimmer illuminance of only 100 lux. As with other SI units, SI prefixes can be used, for example a kilolux (klx) is 1,000 lux.

| Illuminance | Example |
| --- | --- |
| 10$^{-4}$ lux | Total starlight, overcast sky |
| 0.002 lux | Moonless clear night sky with airglow |
| 0.01 lux | Quarter moon |
| 0.27 lux | Full moon on a clear night |
| 1 lux | Full moon overhead at tropical latitudes |
| 3.4 lux | Dark limit of civil twilight under a clear sky |
| 100 lux | Very dark overcast day |
| 320-500 lux | Office lighting |

-continued

| Illuminance | Example |
| --- | --- |
| 400 lux | Sunrise or sunset on a clear day. |
| 1,000 lux | Overcast day |
| 10,000-25,000 lux | Full daylight (not direct sun) |
| 32,000-130,000 lux | Direct sunlight |

In one embodiment, the color and light system of the invention provides for at least one light source to provide a brilliance factor of at least about 2000 lux, at least about 2500 lux, at least about 3500 lux, at least about 5000 lux, at least about 7500 lux, or at least about 10,000 lux. In one embodiment, the color and light system provides about 2000 lux to about 25,000 lux, about 2500 lux to about 20,000 lux, or about 5000 lux to about 15, 000 lux, or about 10,000 lux. Where more than one light source is utilized, each light source may provide at least about 500 lux to about 4500 lux, at least about 1000 to about 4000 lux, or at least about 2000 lux to about 3000 lux, to provide a total lux within the ranges previously recited. Generally, each of the individual colors provides in the same brilliance factor. However, one may choose to have different colors at different lux.

The color and light system of the invention is designed to provide four individual spectral (visible) colors of blue, green, rose pink and peach as described herein. In one embodiment, these colors are provided in a therapy room by four individual light sources (e.g., four individual light fixtures) which are located within a distance so that they can all be viewed at the same time by an individual. In other words, the lights are within a distance from one another so that they do not exceed the subject's peripheral vision.

In one embodiment, the invention provides a therapy room comprising a color and light therapy system as described herein. The room comprises two to four walls and an entrance, wherein the system is positioned in a corner which is located most distant from the entrance. Typically, the walls of the room are white. However, there may be therapeutic benefits to a pale gold or pale blue wall color, which may be selected from among other colors when desired.

In one embodiment, a first set of colors and a second set of colors are positioned on a wall in a color therapy room such that the first set of colors are on a first wall adjacent to a corner in the room and the second set of colors are on a second wall adjacent to the corner. A first set of colors consists of blue and green and the second set of lights consists of the rose pink and peach. Typically, the colors in each of the first and second sets are located in a single horizontal plane and the first and second sets are perpendicular to one another in order to allow each of them to be viewed by a subject simultaneously. In other words, the first set of colors is at a 90 degree angle to the second set of colors. However, other configurations may be selected which allow each of the colors to be used in a subject's therapy to be viewed at the same time.

In one embodiment, each of the four colors is provided by an individual fixture or screen which generates the desired color and lux. In such a case, one can readily design the desired fixture or screen size. For example, in one embodiment, each of the light sources provide about four to about ten square feet in area, or about five to about eight square feet, of each visible light for subjects to observe. This size may be varied as needed or desired. In one embodiment, the visible area of each color is same. In other embodiments, these sizes are varied. Where individual fixtures or screens are utilized, the light sources with the first set and/or the second set may be located within about 0 to 6 inches of each another, or about two to three inches apart, as measured by the distance between the closest edges of the light sources to one another.

In another embodiments, the invention provide for one, two or three fixtures or screens which provide the four colors in a configuration which meets the parameter described herein for four individual light sources. In one embodiment, a screen or other device may provide two, three, or all four of the distinct areas of color as described above.

Suitably, the therapy room permits the subject to be positioned from 18 inches to 6 feet, about three feet, from the first and/or second set of colors. A position at the lower end of this range, or even closer, may be used in order to emphasize the therapeutic effect of a desired color. Alternatively, various positions may be selected to emphasize the therapeutic effect of a single color, a set of colors, blends, or all four colors.

When using the method of the invention, the changes in behavior and focus are felt within the first fifteen minutes. Without wishing to be bound by theory, it is believed this is due to the light penetration from the optical nerved to the frontal lobes. Color light travels so swiftly that absorption changes the brainwaves, e.g., to one of calm and alert focus. Results have been observed that on two occasions non-verbal individuals have said their first work, and reclusive tendencies developed into socializing within thirty minutes.

Empirical Scientific Evidence of the effectiveness of utilizing specific color light therapy (CLT) program applications used as interventions implemented to reduce stress, help focus and calm students and adults with special needs, range from anxiety, Autistic Spectrum Disorders, to cognitive, behavioral, and other disorders, have been successful 1 on a case-by-case basis. In early studies, the success ratio has been in the range of about 15% to 91%, as illustrated in FIG. 1.

Thus, in yet another aspect, the invention provides a method for treating mood, anxiety, attention, substance, and/or behavioral disorders, including without limitation, sunlight affected disorder, depression, modification of circadian rhythms (e.g., sleep pattern disorders, altering sleep patterns for "night owls"), aggression. In still another aspect, the invention provides a method for treating and/or ameliorating the symptoms of an autism spectrum disorder, which may include, one or more of Asperger's syndrome, autistic disorder, Rett's syndrome, childhood disintegrative disorder, and pervasive developmental disorder, not otherwise specified (PDD-NOS). The treatment for each methods comprising positioning a subject to see at least one, at least two, or the four light sources for a sufficient amount of time to provide a therapeutic or mood-altering benefit. In one embodiment, the subject is positioned so as to see blends of a first pair of lights, the second pair of lights, or a blend of the first pair and second pair of lights.

Preferably the treatment is in a therapy room which is white, sunlight gold, or pale blue. For patients having sleep pattern disorders, a pale blue room is preferred. In one embodiment, the method involves exposing a subject to at least one of four lights in the color and light therapy system or blends thereof for at least about 15 minutes, or about twenty to about thirty minutes, or about ten to about 15 minutes. The length of time may be adjusted as needed or initial therapy can be longer at the longer end of this range, or even longer, with maintenance for shorter time periods. For maintenance between therapy sessions, e.g., at home, the therapy may be continued with portable lights which provide the colors provided. Such portable lights may in the form of a helmut with visual interface, a handheld device, light fixtures, or other devices with screens or bulbs of the appropriate color.

In an initial evaluation (diagnostic) or any given therapy session, a subject may be positioned to view all four colors in the therapy room at the same time. Alternatively, a subject may be positioned to view a single color, two colors (e.g., a set), or three colors. Where a subject has previously been diagnosed, a therapy session and/or at home maintenance may involve exposure only to less than all four colors, e.g., a single color, two colors, or three of the colors in the system.

One or more of the four colors may be selected for a therapy session depending upon the desired therapeutic benefit. For example, in one embodiment, the blue color light is useful for inducing calmer behavior and improving focus, and detoxifying chaotic behavior, e.g., in individuals diagnosed with behavioral or learning disabilities. In one embodiment, the green color light is useful for a variety of therapeutic purposes, including promoting physical and emotional balance, e.g., in subjects with discomfort and repetitive motion or speech. In one embodiment, the rose pink light is useful for relaxing the senses of subjects who are over-stimulated and have sensory issues, or become oppositional easily. In one embodiment, the peach light boxes are useful are a variety of purposes including, e.g., in aiding focus and mental clarity, balancing both frontal and temporal lobes, for memory retention and connected communication on current topic being discussed.

In another embodiment, the invention provides four color light sources, which may be fixture or equivalent source, e.g., an LED array, plasma screen or other device. For example, invention utilizes four colors hues in four full spectrum light boxes, each emitting 2500 lux for a total of 10,000 lux, simulating sunlight. The lighting fixtures come in sets of four and are typically a rectangular shape (e.g., rectangle, square). In one embodiment, each light has the ability to be powered off and the color of the filters can be changed, resulting in light of specific wavelengths. Typically, each light fixture contains at least one black light emitting surface (typically where there is a single black light, it is centered) and at least one full spectrum light emitting surface. There are generally located on each side, spaced in equidistance within the area directly behind the light defusing media, colored filter and opening. These two full spectrum light emitting surfaces (bulbs/LED array) are the full height of the interior of the fixture. Each fixture incorporates an interchangeable colored filter media that is seated directly behind the light diffusing media. Behind the black light emitting surface is a reflective surface that is concave in shape hence covering 180 degrees of the rear of the bulb (omitted for LED version). In one embodiment, the fixture is no smaller than 12½ inches wide by 24 inches in height and emits 2,500 lux for each fixture when measured by a lux meter at a distance of 3.5 feet, to provide an illuminance of 10,000 lux when measured by a lux meter at a distance of 3.5 feet when the complete set of four fixtures is used. However, larger sizes may be readily selected. Suitably, each light is equipped with a diffused light aperture having a minimum size of about 1.25 square feet, or in other embodiments a minimum size of about 1.5 square feet, in still other embodiments, a minimum size of about 1.75 square feet, and in other embodiments, a minimum size of about 2 square feet. Alternatively, other types of devices may be used to provide the four hues and illuminance described herein.

The following examples are illustrative of the invention only and are not a limitation of the invention.

EXAMPLES

The inventor found that certain colors of the spectrum needed to be eliminated in order to reduce negative effects. For example, red to red-orange hue was excluded due to a marked excitability, and in some cases hidden rage was remembered. Indigo to purple was eliminated due to a marked difference in superiority and passive aggressive displays of behavior were observed soon after these lights were on for 30 minutes. More particularly, red induced feelings of being "antsy, frantic, or angry", and the purple made them feel "superior or depressed." Therefore these colors were eliminated. Further, the inventor observed and documented that too many varied color wavelengths can cause hyperactivity, erratic behavior, and confusion; this was particularly notable when administering in early studies utilizing seven or more hues in the color light therapy.

Three progressive studies provided the conclusive documentation necessitating the arrangement and hues in the Protocol in the inventor's color light therapy program, proving the need of the elimination of three colors from the seven was necessary (violet, red and yellow.) The final selection of blue, peach, rose-pink and green have proven benefits of calming and focusing individuals who are on the autism spectrum and individuals who present with cognitive impairments.

The number of color and the hues utilized in the four color therapy of the invention provides an improved ability to retain what the individual learns due to being able to focus and remain calm has been documented and observed when the program is administered to children school ages 7-13 years of age before puberty. The elimination of stress bolstered their memory retention. This was also observed and recorded in Dr. Davis' study with Temple students/youths who exhibited high anxiety. (See study with Temple Students, Temple University, Ambler Campus, Pa.)

The inventor's studies have demonstrated that the best results for memory retention were recorded when using the blue and peach light. This was evidenced in the students ability to recite all that transpired in the curriculum taught, whereas other color combinations did not work as well, even if the research individual or student's diet for the last 24 hrs included 2 oz in the AM, and/or 4 oz. at noon, and 6 oz. in the evening of a form of protein. Positing that the cellular structure appears to be responsive to the receptivity of light penetration and proper response with or without nutrition. In every case the ability of each student, with or without being on various medications had positive results in recalling writing and reciting class work.

The studies have revealed the measurable progress and lasting improvements of the four color program, as a stand-alone modality. However, the program may optionally be combined with other therapies, including, e.g., sound therapy, needleless acupuncture, naturopathic nutrition, and neuro-linquistic therapy when warranted. The results provided by the color program have been found to be independent of age, health, or disability, every individual in all of these studies chose the same four color selections as priority out of the seven to nine exhibited.

Example 1

Retrospective Cohort Study in Color Light Therapy

Documentation compiled through surveys of individuals exposed to this four color program of the invention demonstrated a relevant theme for each hue. Consistently and similar responses were narrowed to four colors. Rose Pink: "feel nurtured, warm and loved". Medium Green was selected for its "calming effect on the body or heart". Deep blue, for tranquility and focus. Amber Orange, selected by under and over achievers, each felt "good and empowered". These colors were isolated by the inventor and the experimental research began, concerning how these specific color luminations would affect children and youths with special needs.

Procedure: (After Evaluation of the Individual or Group).

1. Have room ready for individual or group by using only light from the four continuous spectrum lighting, positioned on either side of the furthest corner of the room from the entrance. This positioning immediately brings attention and focus to the light and distracts the individual from what caused the interruption of the activity or original cause of the behavioral disruption, and promotes cessation of those emotions.
2. Determination of the amount of time needed for resetting the focus, is usually 20 minutes to 35, however, more will not be over saturation.
3. Once in the Color Light room, a questionnaire is filled out to determine color selection preference in chronological order. Example: What is your favorite color today? Please list in order: Rose, Green, Sunset Gold or Blue. (See above material). How do you feel now in comparison to when you entered the room?
4. In individual cases a facilitator will ask the questions and write the selection, along with the reason for the need and make the decision if additional color light therapy is needed. In this case a home program for maintenance can be suggested.
5. Progress reports and other complimentary therapies such as sound, vitamin supplementation, needless acupuncture and reevaluation of diet can be decided between the caregiver or the individual can be referred to therapy, for intensive intervention, if needed.
6. Recording the results in percentages for groups and individual success is rated by the amount of those experiencing the program. In every case statistics have shown an improvement from 15 to 91% after the first experience, building up when given consistently on a weekly basis. Determination of daily basis for those with severe problems is made by the data accumulated.
7. Modulation of the colors to fit the facilities criteria is determined and discussed on a monthly basis. Example, one of the light colors may be changed to a muted shade, or additional changes may be admitted to the program.
8. Assimilation of this natural color light is essential for all humans and should be discussed with participants in a preliminary presentation and reported at the end of the term as an encouragement for continuation.
9. Sign out sheets for collecting intervention data to determine amount of students/participants, reason for use and success each felt they received.
10. Equipment replaced when needed, will be determined on a monthly basis. Note: As the individual progresses, their color preference selections may change as needed. An example: A 10 year old diagnosed with anxiety and sensory disorders chose green in his first session. By his third session, his "favorite" color became blue as his first choice. When questioned as to why he changed and how it made him feel, His response was, "I feel good and when I look at blue I think of the ocean, which I love". He is doing so well that his doctors have reduced his need for medication and is now seen once a month instead of weekly visits.

Research data of three independent studies of 153 individuals was complied and recorded. These people were suffering from various mental health disturbances, ranging from poor cognitive skills, medicated, or non-medicated, anxiety disorders, i.e. social anxiety, and panic disorders, individuals within the Autistic Spectrum and college students suffering from depression poor performance anxiety, in facilities, schools, continuing in households provided by participating parents.

All received various methods of color light therapy developing into the final discovery and utilization of the appropriate combinations that aided in delivering calm, focused, and favorable verbal responses in all participants regardless of age or gender.

In all cases the respondents and those who observed recorded and reported the data-now used as empirical scientific evidence, found that the four colored light therapy gave the individual a respite from the causes of mental stress causing despondency—the inability to participate and function well in their community or circle of influence.

The final analysis indicates that it is essential that teachers, parents, and guardians become educated and utilize this research by providing either partial or, in some cases, daily colored light therapy other than what is accepted for seasonal affective disorder.

Figure 2:
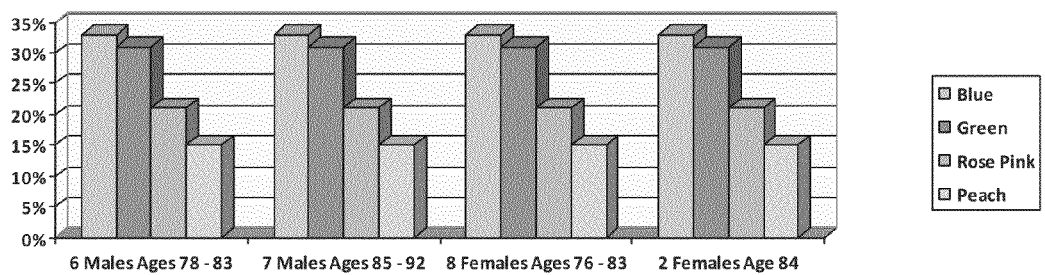
FIG. 2 is a bar chart illustrating the results of Study 1, where for each grouping, the first bar represents blue, the second represents green, the third represents rose pink, and the fourth represents peach.
Figure 3:
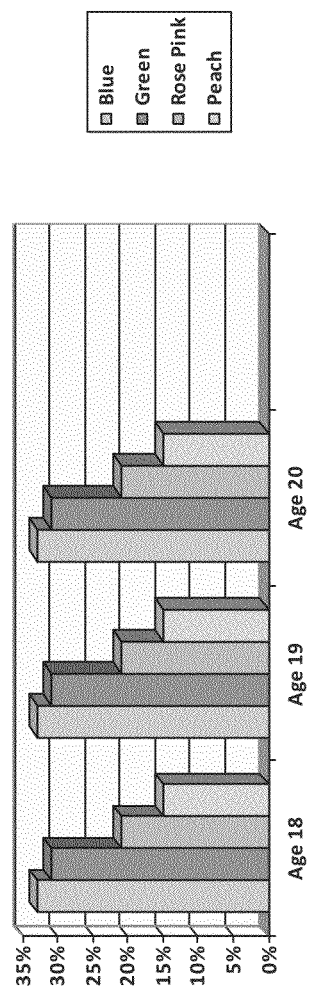
FIG. 3 is a bar chart illustrating the results of Study 2, where for each grouping, the first bar represents blue, the second represents green, the third represents rose pink, and the fourth represents peach.

Study #1: Richboro Health Care Center
  Population Maximum, 50 seniors, ages 73-90.
    A collaborative agreement was signed by Richboro Health Care Center, in Richboro, Pa., on Nov. 18, 2004, for a short term, 90-day study of Color Light Therapy divided into monthly visits for residents who were the most problematic and for the overall population.
Participants: 23 seniors all on medication for cognitive disorders from dementia to severe Alzheimer's disease.
  6 males, ages 78-83
  7 males, ages 85-92
  8 females, ages 76-83
  2 females, aged 84
Assistants: One videographer, two Color Therapists, one Body Worker, and a Recording Secretary.
Equipment: Set up table, video camera.
  Four Colored Gels (Orange, Pink, Green, and Indigo) each measuring 24"×36" were placed on windows in front of the residents.
  A small portable full spectrum light 150 watts with five interchangeable hues of Red, Violet, Aqua, Gold and Teal were shone straight ahead in five minute intervals.
Process:
  Participants were chosen for their geriatric chronological distresses caused by cognitive decline seen in aging from mild to major dysfunction, and in some cases refusal to adjust to the socialization within this community.
  Residents were brought into the community room. Approximately 23-25 residents attended the program presentation. Some were on pallets, others in wheelchairs, and others assisted. All were medicated according to their disorders. The only participants that were not were the staff attendants, the inventor, and her assistants.
  The inventor gave a presentation and spoke to the residents and presented the 30 minute program while interacting with those who became responsive. To the amazement of the professional staff in attendance, even those in a stupor rallied after 10-15 minutes of color light therapy. At this juncture, the inventor began to ask the questions which have become the standard in the program:
    Which color do you like best?
    Why?
    How does it make you feel?
    Pick the next three.
    Which do you dislike?
  After all the colors were shone through either natural light emanating from the windows or from the full spectrum light, participants were asked to pick which light made them feel different and in what respect. After the presentation, the residents asked if the inventor would come back, and if she could stay longer with the lights because they felt better.
  After the initial visit, the inventor was asked if she would administer the program to those who were bedridden or antisocial with behavioral issues in their rooms. The inventor consented, and the results were astounding. One resident in particular, a gentleman, had mattresses placed the floor all around his bed, his one hand was in restraints to prevent injury to him or others.
  When the inventor asked if she could enter his room, he refused at first, but she persisted by asking if she could just show him colored lights and asked if he would consent to have a video of him made. He did consent and became amenable after 5 minutes of color light therapy, using blue, pink and green, within that time span. Result: Subject was socializing with the inventor and her staff and asked them to stay.
  Progress reports of each visit were recorded. The calm and relaxed behavior of the residents lasted approximately two to three days depending on the amount of medication each individual was ingesting. The inventor was asked to prolong the study, due to the positive outcome. The long lasting results are remarkable, recorded on video and compiled and documented. FIG. 2 provides the results of Study 1.
Study #2: Temple University Ambler Campus:
  Ambler, Pa.
  Because the Efficiency Standardization is now clearly defined for those suffering from cognitive neurological disturbances, the inventor decided on a second study with youths who were active, healthy, mentally productive college students for a comparison. Now using the condensed and modified version with colors that proved to be the most calming, restoring alertness, and focus she was invited to Temple University.
Participants: 53 College students, age range 18-20.
Equipment: One small portable full spectrum light.
  Colored Gel Filters: Dark Green, Medium Green, Indigo, Cobalt Blue, Magenta, Rose Pink, Orange, and Gold.
  Questionnaires, pens
Process:
  Each Student individually approached the table, where the inventor, administered the colored light therapy, starting with the green in sequence and ending with gold. Each student was asked to select their choice of color from one to four with one being the favorite and four the least favorite. Questions in the survey taken were as in the first study, asked and recorded on the questionnaires, dated, and signed.
    Colors chosen: Sunrise—cobalt blue and peach
    Sunset—rose pink and medium green
Result:
  Each student opined that they felt calm, relaxed, and could focus better. The graph in FIG. 3 below illustrates the measurable outcome from the surveys taken.

Example 2

Four Color Light Therapy Process

In the examples provided below, the invention utilizes four colors hues in four full spectrum light boxes, each emitting 2500 lux for a total of 10,000 lux, simulating sunlight. The lighting fixtures are rectangular and come in sets of four, each having the ability of being powered off as well as the changing of the color of the filters, resulting in light of specific wavelengths. Each light fixture contains one centered black light emitting surface (6 watt bulb or similar LED array) with one full spectrum light emitting surface (85 watt bulb or similar LED array) on each side, spaced in equidistance within the area directly behind the light defusing media, colored filter and opening. These two full spectrum light emitting surfaces (bulbs/LED array) are the full height of the interior of the fixture. Each fixture incorporates an interchangeable colored filter media that is seated directly behind the light diffusing media. Behind the black light emitting surface is a reflective surface that is concave in shape hence covering 180 degrees of the rear of the bulb (omitted for LED version). The fixture should be no smaller than 12½ inches wide by 24 inches high and emitting 2,500 lux for each fixture and an illuminance of 10,000 lux for the complete set of four fixtures, when measured by a lux meter at a distance of 3.5 feet. The defused opening is 9⅝ inches wide by 21½ high and is framed to allow access to the interior of the fixture. The fixture allows for easy and quick changing of the filter media. Each light emitting surface has an electronic or electromechanical device (ballast/LED driver) to provide the appropriate amount of electrical current at the voltage needed. Each light is equipped with a diffused light aperture of 21½×9⅝ with an area of about 207 square inches (206.9375). In one embodiment, this is the minimum size. However, in another embodiment, the size may range from 207 square inches±10% or larger.

In the studies described below, two sets of color light boxes are viewed together. The first three colors combined make white light; however, when used with full spectrum individually and combined according to the resulting studies, the therapy has measurable success in every case and lasting to permanent effects when used consistently on a daily basis. Two full spectrum light colors depict sunrise, two others sunset. Thus covering the differences of circadian rhythms between the night or day personal biological clock.

Study #3:

Four Color light boxes as described above were utilized in sets of two, and hung in alignment assimilating sunrise and sunset creating an atmosphere of nature's hues. The colors utilized are the Sunrise-colors chosen above (cobalt blue and peach), and the Sunset colors chosen above (rose pink, and medium green.)

The Individuals measurable progress is documented over time periods of minimally four to ten sessions ranging four to ten months, and providing progress reports after each of their bi-monthly sessions. Each session is approximately 20 to 30 minutes in duration.

All individuals are asked the same questions upon entering the Color Therapy Room:

Please choose the colors on a scale of one to four, one being your favorite, two your second favorite, third, and fourth your least favorite.

Can you explain why you chose these colors in order of preference?

All of the answers are recorded and evaluated by the inventor.

Blue and Yellow Orange Simulate Sunrise:
Purpose: to reset the biological clock

The color combinations of Green and Rose Pink are placed together approximately 6 to 8" apart, to assimilate a sunset, total lux. Of each light box 2500 lux=5000 lux per set for a total of 10,000 lux, equivalent to the Sun without the UV rays due to the diffusers in the color lens and filters.

Observing that within a decade the tremendous escalation of children born with Autism and hearing the outcry for help as the numbers changed from one out of 500 to one in one hundred (and climbing), the inventor began the third study.

All material presented utilizes the collective work of the two studies as we enter the third phase and final study encompassing children and youths, ages 3-18 years of age with Down Syndrome and those within the Autistic Spectrum. Twenty three individuals with special needs were brought in though referrals by their primary physicians, teachers, case workers, and parents.

Nineteen of these were diagnosed with varying degrees of Autism, from mild to severe. Two were non-verbal and were in families where one or more siblings diagnosed within the Autistic spectrum.

Process:

A colored light therapy room was created as described herein. The room was devoid of all light other than the light at the entrance, by shades and curtains that also accentuate the hues selected. The inventor placed both a body work table (for those who cannot sit) and a chair which is positioned 3.5 feet from the lights between the second and third light box. This allows all the wavelengths to converge simultaneously into the left and right eye-photoreceptors. The combination of wavelengths from each hue begins to calm the individual within about five minutes.

The questions were asked and recorded, and for the non-verbal children, they point or hug their favorite light box. In one case, a seven-year old non-verbal boy with severe ASD came in reluctantly. But, after five minutes he approached the rose pink light and said his first word, "home", to the amazement of his father. The father became quite overwhelmed emotionally, explained with immense gratitude that this was his son's first word, and continued to tell the inventor that she didn't understand what this meant for them.

This same young boy then proceeded after 20 minutes of color light therapy to walk and socialize with a Down syndrome child, and wanted to stay. This reaction is prevalent in that once the color light therapy is experienced, the individual doesn't want to leave. When asked why, invariably they express joy, and say they feel better and want to stay that way.

In behaviorally challenged youths, the four color system combination elicits a non-oppositional response. They articulate expressively, respond to questions appropriately and take directives without complaint. Focus and perception is accurate whether they are on or off medication. Responding to others in the room socially when they had exhibited antisocial behavior prior to treatment is reported through progress reports in all mild to high functioning Autistic children and those with Pervasive Development Disorder (PDD).

Reshaping perception by first allowing the biological clock to be reset though the balancing effects of the light program administered in the therapeutic room and then maintained in the youth's home has shown progressive successful outcomes. Parents report that the child accepts authority without tantrums or opposition previously displayed before color light therapy. Performing tasks, homework, selecting clothing, washing, cleaning their area, helping with chores, and having a clearer understanding of what is expected of them without anxiety has been well documented. Long lasting effects, of focus and concentration for classroom and home study has brought this therapy combination to the positioning of the present necessity of patenting the program.

Evidence of each individual remaining in their seat, holding meaningful conversation and articulating words connectively pertinent to the subject matter is impressive. This is especially true for those youths who, prior to the program and color light, were demonstrating repetitive behavior and tantrum or abusive gestures seen as obsessive compulsive disorder or PDD.

Measurable outcome of the individual's selection of Spectral primary colors in consecutive order of favorable preference from 1 to 4 (1 being the most favorable and 4 being the least favorable):
Blue light Luminance—HID (high in density) Is Measured in Nanometers
Wavelength=500 nm. 33% chose Blue as their primary.

The method of the invention utilizes blue light boxes as potent frequency to induce calm and focus, detox chaotic behavior and stabilize each individual diagnosed by referring health care professionals or educators as having behavioral or learning disabilities.
Green Light Luminance
Wavelength=550 nm. 31% chose Green as their secondary.

Green light boxes promote physical and emotional balance, as observed after administering to individuals with discomfort and repetitive motion or speech.
Rose Pink Light Luminance
Wavelength=545 nm. 21% chose Rose Pink as their third.
Rose Pink light boxes relax senses of those who are over stimulated and have sensory issues, or become oppositional easily.
Peach Light Luminance
Wavelength=600 nm. 15% chose Peach as their fourth.

Peach light boxes (a blend of gold, yellow and orange), aid focus and mental clarity, aids in balancing both frontal and temporal lobes, for memory retention and connected communication on current topic being discussed.

These colored lamps can each stand alone for their effectiveness in Chromo-therapy, as non-invasive and concise properties for the described distresses.

Using the sunrise two-color and the sunset two-color processes separately or together to reset our biological clock is proving to be beneficial to every participant in promoting better mental health. In some cases, parents feel that they have their children returning to a normal approachable state of mind and body.

This unique process combines special enhancements when necessary according to the individual needs but stands alone as the prime source to rebalance and reset the biological clock of those suffering from Autism and other special needs as witnessed in these studies.

Summation of Measured Outcomes:

Three progressive studies provided the conclusive documentation necessitating the arrangement and hues in the process and protocol in our color therapy program. The studies proved the elimination three colors of the seven color system described by others was necessary (violet, red, and yellow colors.) The final selection of four colors has proven benefits—for the distracted, confused, and cognitive impaired mind far greater than a seven or nine color illumination therapy.

Utilizing the natural solar cycles of sunrise and sunset indoors, in an age where productivity and recreation are accelerated by the computer and electronic games is imperative to maintaining total wellness.

In many cases, too many color varied wavelengths can cause hyperactivity, erratic behavior, and confusion as observed when administering seven or more hues of light therapy. The greater benefit is documented and observed when the program is administered to children school ages 7-13 years of age before puberty. Also in youths exhibiting high anxiety, as recorded in a second study at Temple University, Ambler Campus, Pa.

Thus, the second study showed no variation of the receptivity of the lights, only in selection of prioritizing of hues (in either, gender or age as compared to the first study.)

The first study's lasting measurable effects produced scientific empirical evidence in each facility, where professional staff and caregivers recorded progress, resulting in requests to return to the facility once a month for four months.

The third and final study reveals the measurable progress and lasting improvements of the four color process, as a stand-alone modality. When warranted tonation-sound therapy, needleless acupuncture, naturopathic nutrition, and neuro-linguistic therapy can be utilized in tandem with the Bio-logical Clock four color light therapy program.

Overall combing these methods for severe cases produce the most dramatic results.

What the inventor found is that regardless of age, health, issue, or disability every individual in all of these studies chose the same four color selections as priority, out of the nine exhibited.

Example 3

Three Track Format—Four Colored Spectral Protocol

Regardless of the medical diagnosis or causation, the stabilization of the method of the invention in a three track format has been found to be consistently beneficial.

A. Age Groups 2-7, with Diagnosis of ADD, ADHD, PDD, NOS, Downs Syndrome or Other. Track 1:

First session for light program, by introducing each color for 3 minute sessions for a total of 12 minutes. Beginning with Blue to promote calm and focus, then the partner Peach to maintain alertness, followed by the Rose Pink, for receptivity, and then the Green to enforce the proper physical acceptance.

This is repeated until the child can express by pointing or verbally choosing their favorite colors in order from first to last. The time is increased by one minute in each session until a total of 20 minutes is sustained. Each session is recorded and documented as to acceptance and measured outcome.

B. Age Groups 8-12—with Challenges as Mentioned in Track I, Moderate to Severe Autism or Other Challenges (CDD, PDD, Rett's Syndrome, ADD, ADHD, NOS), Track 2:

After initial assessment from prior medical diagnosis and observations by school psychologists in the individuals records, parental goals and an education of the format on our four colored light therapy is decided by the therapist. All begin with a minimum of 10 sessions, starting with 5 minutes and increasing to 20 minutes. Each colored light is turned on separately beginning with the Blue and ending with Green as tolerated by the individual, until all four are illuminated, then an additional 10 minutes are spent in the light room. All illumination in the light therapy room is within about 3 feet to about 4 feet from the light source.

The first four sessions are administered on a weekly basis. As the individual shows progressive improvement, the final six sessions are on a bi-monthly basis. Improvement percentages vary according to tolerance and whether there is medication involved by their primary physicians. These tracks may overlap or be repeated as needed.

All are non-invasive and as documented, consistently show high percentages of measured outcomes. In some cases, the individual has had progress such that they have been maintstreamed.

C. Age Group 13-23, with Severe Challenges of ODD, PDD, ADD, ADHD, NOS as Diagnosed by their Primary Care Physicians. Track 3:

In this track, tracks one and two are repeated and all four colored lights are administered simultaneously.

Due to the complexity of each individual's diagnosis, the assessor determines which of the two tracks should be escalated with additional intervals of the four colored light therapy, both individually and collectively. Additionally, the parent or caregiver is given instruction on proper nutrition, vitamin supplementation and the positioning of the individual (in case there is the need for restraint/holding the individual while light therapy is being administered.) Here the cycles of tracks one and two are repeated and lapsed into daily intervals beginning with 5 minutes and increasing to what is best tolerated (optimally reaching 15-20 minutes, at least three times a day.) In these cases the need for replication is seen as beneficial, as the brain syncs to its natural biological state; this has been shown to be successful in this continuous application. This assimilation of four colored frequencies mimics natural sunrise and sunset, and has been proven to be indispensable to these individuals and the entire family, resulting in manageability of their challenges.

Example 4

Further Case with Four Colored Spectral Protocol

A. JR is an 11 year old Male that had been diagnosed with PDD and NOS due to his maternal mother being addicted to drugs while in utero. When first seen, JR was non-communicative, demonstrative and very underweight and small for his age. He would not have direct eye contact or speak directly. When he did speak it was so soft you could almost not hear him. He was getting poor grades, 67-70 average in all subjects and was being threatened with expulsion. In the last 10 months JR has had 11 therapy sessions. He has shown a measured outcome improvement of 78% in communication. His grade point average has risen to 87-95. JR's social skills have improved as well and his ability to give oral reports. The colored light therapy of the invention has used has "reset his biological clock", enabling him to sleep 8 hours a night and to increase his appetite. Before and after pictures show his remarkable improvement.

B. BB is a 15 yrs old Male that has been diagnosed with ADHD and NOS due to his premature birth and mild cerebral palsy. He has been seen since his birth. In the last 10 months BB has had 12 Therapy sessions. He has shown a measured outcome of 67%. Due to the four colored light therapy he has reset his biological clock enabling him to emotionally improve, demonstrating no tantrums and being accepted by his peers.

C. LM, is a 15 yrs old Female that has Down Syndrome and has been diagnosed with, behavior disorder and Tardif Dyskinesia due to taking too many medications to keep her manageable. All these efforts failed and she was continuously threatened with expulsion. Her behavior continued to be aggressive to her classmates and the school was going to stop her from attending public school and the parents were looking into an institution.

In the last 10 months, LM has had 10 color therapy sessions. She has shown a measured outcome improvement of 40% in communication skills, and she will remain in school without expulsion due to improvement in behavior. She is also now able to participate in community activities and games and has shown a decrease in Tardif Dyskinesia disorder.

He

D. DI is a 9 yrs old Male that has been diagnosed with NOS. He is emotionally stressed and demonstrates performance anxiety. He has had 10 color therapy sessions. He has shown a measured outcome of 67%. Due to the four colored light therapy he has reset his biological clock enabling him to emotionally improve, demonstrating no tantrums and being accepted by his peers.

E. AV is a 7 yrs old Male that has been diagnosed with ADHD and OSCD. AV has shown a measure outcome of 61%. After 13 months of light therapy treatment, AV has grown 35 inches in size and has become calm and focused.

F. AA is a 2 year old male that has been diagnosed with PDD and NOS. He has shown a measured outcome of 33%. After 4 treatments of light therapy in a 2 month period, he has shown a big improvement in communication, responsiveness and eye contact. Overall, AA is following directions better and is interacting with family and peers more often. AA's mother reports that he is also much more affectionate.

G. CM is a 7 year old, male that has been diagnosed with Tourette's Syndrome. He has shown a measure outcome of 57%. After 3 treatments over a 3 month period, he has shown decrease in tic disorder and communicates without prompting.

H. ET is a 10 year old female that is non verbal and has Down Syndrome. She has shown a measure outcome of 60%. After 4 treatments over a 3 month period, she has shown improvement in understanding by her example of starting piano lessons, shows more signs of interaction and verbal communication with peers and family and improvement in balance. She also is now sleeping through the night.

I. LM is a 21 year old female that has been diagnosed with anxiety/depression and self injurious behavior. She has shown a measured outcome of 50 to 70%. She has improved in mental calmness and ability to focus on school and work. She has also stopped self injurious behavior.

All publications, patents and patent applications, cited in this specification are incorporated herein by reference. While the invention has been described with reference to particularly preferred embodiments, it will be appreciated that modifications can be made without departing from the spirit of the invention.

The invention claimed is:

1. A color therapy room comprising four walls which are pale gold in color, an entrance, and a spectral color and light therapy system useful in treating and/or ameliorating the symptoms of an autism spectrum disorder in a subject in need thereof, said spectral color and light therapy system consisting of four different lights in a first and a second pair which emit colored light at a combined total brilliance factor of 2000 LUX to 25,000 LUX, wherein a first light in the first pair of lights provides (a) (i) blue light in the range of 450 to 475 nm; and a second light in the first pair of the lights provides (ii) green light in the range of 495 nm to 570 nm; and a third light which is in the second pair of lights provides a light of 635 nm to 650 nm; and a fourth light which is in the second pair of the lights is 580 nm to 610 nm;

wherein each of the lights emits spectral color in the absence of non-visible light below 390 nm or above 750 nm, and wherein the first pair of lights and the second pair of lights are positioned on the walls in the color therapy room such that the first pair of lights are on a first wall adjacent to a corner in the room and the second pair of lights are on a second wall adjacent to the corner.

2. The room according to claim 1, wherein the subject is positioned from 18 inches to 6 feet from the first and/or second pair of lights.

3. The room according to claim 1, wherein the room includes a location three feet from the first and/or second pair of lights.

4. The room according to claim 1, wherein each of the lights is emitting at a brilliance factor of 500 LUX to 4500 LUX, at a brilliance factor of 1000 to 4000 LUX, or at a brilliance factor of 2000 to 3000 LUX.

5. The room according to claim 1, wherein the first pair of lights is at a 90 degree angle to the second pair of lights.

6. The room according to claim 1, wherein each of the lights provide four to ten square feet in area of visible light for subjects to observe or five to eight square feet in area of visible light for the subjects to observe.

7. The room according to claim 6, wherein each of the lights is the same size.

8. The color therapy room according to claim 1, wherein the system is positioned in a corner which is located most distant from the entrance.

* * * * *